United States Patent [19]

Bauer et al.

[11] Patent Number: 5,320,969
[45] Date of Patent: Jun. 14, 1994

[54] METHOD, COMPOSITION AND DEVICE FOR THE SEMIQUANTITATIVE DETERMINATION OF SPECIFIC GRAVITY OF A TEST SAMPLE

[75] Inventors: Robert Bauer, Bristol; John A. Cattell, Elkhart, both of Ind.

[73] Assignee: Miles Inc., Elkhart, Ind.

[21] Appl. No.: 143,530

[22] Filed: Oct. 27, 1993

Related U.S. Application Data

[63] Continuation of Ser. No. 964,876, Oct. 22, 1992, abandoned.

[51] Int. Cl.⁵ .................. G01N 33/20; G01N 31/22
[52] U.S. Cl. .................................. 436/84; 422/56; 422/57; 436/74; 436/79; 436/169
[58] Field of Search ............... 422/55, 56, 57, 58; 436/66, 73, 74, 79, 84, 169, 170

[56] References Cited

U.S. PATENT DOCUMENTS

| | | | |
|---|---|---|---|
| 3,975,161 | 8/1976 | Svoboda et al. | 436/66 |
| 4,076,502 | 2/1978 | Dugle et al. | 422/58 |
| 4,473,650 | 9/1984 | Wang | 436/169 X |
| 4,532,216 | 7/1985 | Wang | 436/169 X |
| 4,587,220 | 5/1986 | Mayambala-Muranika | 436/66 |
| 4,871,679 | 10/1989 | Tanaka et al. | 436/170 X |
| 4,959,305 | 9/1990 | Woodrum | 436/170 X |
| 4,960,710 | 10/1990 | Lau | 436/169 X |
| 4,966,784 | 10/1990 | Tanaka et al. | 436/79 X |
| 5,055,407 | 10/1991 | Lau et al. | 436/169 X |
| 5,064,625 | 11/1991 | Mangold et al. | 436/169 X |
| 5,087,575 | 2/1992 | Lau | 436/169 X |
| 5,089,420 | 2/1992 | Albarella et al. | 436/169 X |
| 5,106,752 | 4/1992 | Mangold et al. | 436/169 X |

*Primary Examiner*—James C. Housel
*Assistant Examiner*—Mihon I. Cano
*Attorney, Agent, or Firm*—Roger N. Coe

[57] ABSTRACT

A method, composition and test device for the semi-quantitative determination of specific gravity of a test sample are disclosed. The method utilizes a reagent composition capable of producing a detectable and measurable response that correlates to the concentration of cations, and therefore the specific gravity, of the test sample. The reagent composition comprises: a) a polyvalent metal ion having a valence of at least two, like mercuric ion or calcium ion; b) an indicator capable of interacting with the polyvalent metal ion to provide a polyvalent metal ion-indicator complex having a first color; c) a buffer; and d) a suitable carrier. The reagent composition is used in a wet phase specific gravity assay or is incorporated into a carrier matrix, like filter paper, to provide a test pad useful in a dry phase specific gravity assay of a test sample, such as urine.

25 Claims, No Drawings

METHOD, COMPOSITION AND DEVICE FOR THE SEMIQUANTITATIVE DETERMINATION OF SPECIFIC GRAVITY OF A TEST SAMPLE

CROSS-REFERENCE TO RELATED APPLICATION

This is a continuation of U.S. application Ser. No. 07/964,876, filed Oct. 22, 1992, now abandoned.

FIELD OF THE INVENTION

The present invention relates to a method, composition and test device for the semiquantitative determination of specific gravity of a test sample. More particularly, the present invention relates to a semiquantitative method of assaying an aqueous test sample, such as urine, for specific gravity utilizing a reagent composition that undergoes a detectable or measurable response as a result of contact between the test sample and the reagent composition, wherein the response is essentially independent of test sample pH. The detectable response is proportional to the cation concentration of the test sample and can be correlated to the specific gravity of the test sample. The reagent composition provides sufficient color differentiation between test samples having different specific gravities to provide a semiquantitative assay for the specific gravity of the test sample.

BACKGROUND OF THE INVENTION AND PRIOR ART

The specific gravity of a test sample, such as urine or serum, is a measure of the relative proportions of solid material dissolved in the test sample to the total volume of the test sample. In general, the specific gravity of a test sample is a measure of the relative degree of concentration or the relative degree of dilution of the test sample. With regard to urine samples, the assay for specific gravity, either quantitative or semiquantitative, helps interpret the results of the other assays performed in a routine urinalysis.

Clinically, under appropriate and standardized conditions of fluid restriction or increased fluid intake, the specific gravity of a urine sample measures the concentrating and diluting abilities of the kidneys of an individual. The specific gravity of urine ranges from about 1.005 to about 1.030, and usually is in the range from about 1.010 to about 1.025. A specific gravity of about 1.025 or above in a random first morning urine specimen indicates a normal concentrating ability of the kidneys.

Either an abnormally low or an abnormally high urine specific gravity is clinically significant. Therefore, accurate and reliable specific gravity assays of urine and other aqueous test samples must be available for both laboratory and home use. The assays must provide an accurate measurement of abnormally low and abnormally high specific gravities, such that a correct diagnosis can be made and correct medical treatment implemented, monitored and maintained.

For example, diabetes insipidus, a disease caused by the absence of, or impairment to, the normal functioning of the antidiuretic hormone (ADH), is the most severe example of impaired kidney concentrating ability. This disease is characterized by excreting large urine volumes of low specific gravity. The urine specific gravity of individuals suffering diabetes insipidus usually ranges between 1.001 and 1.003. Low urine specific gravity also occurs in persons suffering from glomerulonephritis, pyelonephritis, and various other renal anomalies. In these cases, the kidney has lost its ability to concentrate the urine because of tubular damage.

An abnormally high urine specific gravity also is indicative of a diseased state. For example, the urine specific gravity is abnormally high in an individual suffering from diabetes mellitus, adrenal insufficiency, hepatic disease or congestive cardiac failure. Urine specific gravity likewise is elevated when an individual has lost an excessive amount of water, such as with sweating, fever, vomiting, and diarrhea. In addition, abnormally high amounts of nonionic urinary constituents, like glucose and protein, increase the urine specific gravity to 1.050 or greater in some individuals suffering from diabetes mellitus or nephrosis. Urine with a fixed low specific gravity of approximately 1.010 that varies little from specimen to specimen is known as isothenuric. This condition is indicative of severe renal damage with disturbance of both the concentrating and diluting abilities of the kidney.

In order to determine if an individual has either an abnormally high or an abnormally low urine specific gravity, and in order to help monitor the course of a medical treatment to determine its effectiveness, simple, accurate and inexpensive specific gravity assays have been developed. In general, the specific gravity of a test sample is a measurement that relates to the density of the test sample. The specific gravity is a value derived from the ratio of the weight of a given volume of a test sample, such as urine, to the weight of the same volume of water under standardized conditions (Eq. 1).

$$Sp.\ Gr. = \frac{\text{weight of urine}}{\text{weight of water}} \qquad \text{Eq. 1}$$

Water has a specific gravity of 1.000. Since urine is a solution of minerals, salts, and organic compounds in water, the specific gravity of urine is greater than 1.000. The relative difference reflects the degree of concentration of the urine specimen and is a measure of the total solids in urine.

Several methods are available to determine the specific gravity of urine. The most widely used method, and possibly the least accurate, employs a urinometer. The urinometer is a weighted, bulb-shaped instrument having a cylindrical stem containing a scale calibrated in specific gravity readings. The urinometer is floated in a cylinder containing the urine sample, and the specific gravity of the urine is determined by the depth the urinometer sinks in the urine sample. The specific gravity value is read directly from the urinometer scale at the junction of the urine with the air. The urinometer method is cumbersome and suffers from the disadvantages of: a) requiring large volumes of urine test sample, b) a difficult and inaccurate reading of the urinometer scale, and c) unreliable assays because the urinometer is not regularly recalibrated.

Refractometry provides an indirect method of measuring the specific gravity of urine. The refractive index of urine is directly related to the number of dissolved particles in urine and, therefore, is directly related to the specific gravity of urine. Consequently, measurement of the refractive index of urine can be correlated to the specific gravity of urine. The refractometer method of determining urine specific gravity is desirable because specific gravity measurements are performed on as little as one drop of urine. However, the refractometer has the disadvantages of requiring daily calibration and not being amenable to home assays.

The falling drop method is another method of assaying for specific gravity which, like the urinometer, directly measures urine specific gravity. In this method, a drop of urine is introduced into each of a series of columns filled with solvent mixtures of increasing and known specific gravity. When the drop of urine comes to rest after its initial momentum has dissipated, and then neither rises nor falls, the specific gravity of the urine is determined to be identical to the specific gravity of the solvent mixture of that particular column. The falling drop method, however, is not widely used in routine urinalysis because of the lengthy time requirements in setting up such a assay and the inability of an individual to perform the assay at home.

The falling drop method described above also can be performed instrumentally. The instrument-based assay uses a specially designed column filled with a silicone oil having a controlled specific gravity and viscosity. The column is designed to measure the time required for a precisely measured drop of test sample to fall a distance defined by two optical gates (lamp-phototransistor pairs) mounted one above the other in a temperature-controlled column filled with a water-immiscible silicone oil of a slightly lower density than the test sample. The falling time is measured electronically and computed into specific gravity units. This specific gravity method is very precise, but the cost of the assay instrument and the degree of skill required to operate the instrument makes home testing for urine specific gravity impractical.

Not one of the above-described specific gravity assay methods is suited to performing specific gravity assays outside a medical office or laboratory. Consequently, reagent impregnated test strips were developed to enable an individual to perform specific gravity assays at home. In general, the test strip assay developed for specific gravity determinations is an indirect assay method, wherein the test strip changes color in response to the ionic strength of the urine sample. The ionic strength of a test sample is a measure of the type and amount of ions present in a test sample. The specific gravity of a test sample is proportional to test sample ionic strength. Therefore, by assaying for the ionic strength of a test sample, the specific gravity is determined indirectly by correlating the ionic strength of the test sample to the specific gravity of the test sample.

The present day specific gravity test strips are pH dependent, and comprise a carrier matrix impregnated with a reagent composition including a polyelectrolyte, such as a partially neutralized poly(methyl vinyl ether/maleic acid); a chromogenic indicator, such as bromothymol blue; and suitable buffering agents. The reagent composition is sensitive to the number of ions, or electrolytes, in the test sample, such that the polyelectrolyte of the reagent composition undergoes an ion exchange, and releases hydrogen ions into the test sample solution in exchange for cations present in the test sample in an amount relative to the ionic strength of the urine sample.

Therefore, as the concentration of electrolytes in urine increases (high specific gravity), more cations are available to exchange with hydrogen ions present on the polyelectrolyte of the reagent composition. The overall result is a release of hydrogen ions into the urine sample, and a resulting pH decrease of the urine sample that causes a color transition of the bromothymol blue chromogenic indicator from blue-green to green to yellow-green in response to increased specific gravity. The resulting color transition, indicating a pH change caused by increasing ionic strength, i.e., increasing specific gravity, is empirically related to the specific gravity of the urine sample.

For test strips utilizing the partially neutralized poly(methyl vinyl ether/maleic acid) polyelectrolyte and bromothymol blue indicator, assays for specific gravity are performed on aqueous test samples having a specific gravity of about 1.000 to about 1.030. A reading of 1.000, or a blue-green color, indicates that the urine has a very low specific gravity, as demonstrated by the lack of a color transition of the chromogenic indicator dye. A specific gravity reading of about 1.005 to about 1.030 is signified by color transitions, from blue-green through green to yellow-green, that serve as reliable indicators of increasing specific gravity.

In accordance with the present day reagent strip method, an individual can readily determine, visually, the specific gravity of a urine sample in the range of about 1.000 to about 1.030. However, the presently available commercial test strips are pH dependent and utilize a pH indicator. Accordingly, the assay is partially affected by the pH of the urine sample. Therefore, it is desirable to provide a method of determining urine specific gravity that is essentially independent of urine sample pH, such that an accurate specific gravity assay can be interpreted in conjunction with assays for other urine analytes to provide a reliable diagnosis and to allow initiation of a correct medical treatment.

It would be extremely advantageous to have a simple and trustworthy method of assaying for urine specific gravity that allows visual differentiation of specific gravity values from about 1.000 to about 1.035. By providing a semiquantitative method of determining urine specific gravity in an easy to use form, such as a dip-and-read test strip, the urine assay can be performed by laboratory personnel to furnish immediate test results. The semiquantitative specific gravity assay results can be interpreted in conjunction with assays for other urine constituents, such that a diagnosis can be made without having to wait for assay results and a medical treatment can be commenced immediately. Furthermore, the test strip method can be performed by an individual at home to semiquantitatively determine the specific gravity of the urine and therefore to help monitor the success of the medical treatment the individual is undergoing.

As will be described more fully hereinafter, the method of the present invention is essentially independent of test sample pH and allows the fast, semiquantitative assay for specific gravity of urine and other aqueous test samples by utilizing a reagent composition comprising a polyvalent metal ion having a valence of at least two; an indicator capable of interacting with the polyvalent metal ion to provide a polyvalent metal ion-indicator complex having a first color; and a buffer. The reagent composition provides sufficient sensitivity and sufficient visual color differentiation between urine samples to yield semiquantitative specific gravity assays. In addition, urine specific gravities of about 1.000 to about 1.035 can be determined quickly.

Any method of assaying for the specific gravity of urine or other aqueous test samples must yield trustworthy and reproducible results by utilizing a reagent composition that undergoes a color transition in response to the specific gravity of the test sample, and not as a result of a competing chemical or physical interaction, such as a pH change or preferential interaction with another test sample component, like protein or glucose. Additionally, the method and composition utilized in the specific gravity assay should not adversely affect or interfere with other test reagent pads that are present on multiple test pad strips.

In accordance with the present invention, the reagent composition can be incorporated into a carrier matrix to provide sufficient sensitivity and color differentiation to assay for cation concentration, and therefore for specific gravity between about 1.000 to about 1.035. In addition, although dry phase test strips have been used to assay for specific gravity, no dry phase test strip has incorporated a polyvalent metal ion; an indicator capable of interacting with the polyvalent metal ion to provide a polyvalent metal ion-indicator complex having a first color; and a buffer in a semiquantitative assay for specific gravity of a test sample.

Prior patents disclose the polyelectrolyte-dye ion exchange chemistry presently utilized in the specific gravity assay of urine. For example, Falb et al. U.S. Pat. No. 4,318,709 and Stiso et al. U.S. Pat. No. 4,376,827 disclose a polyelectrolyte-dye technique used to assay for urine specific gravity. Each patent teaches utilizing polyelectrolyte-dye chemistry to determine the specific gravity of urine by monitoring the color transition of the dye.

The Falb et al. and Stiso et al. patents each disclose a composition and a method wherein the cations present in the test sample induce an ion exchange with the polyelectrolyte, thereby introducing hydrogen ions into the test solution. The change in hydrogen ion concentration, i.e., pH, is detected by a pH indicator. Accordingly, the previously disclosed methods are sensitive to the pH of the aqueous solution.

The composition and method of the present invention differ from the above disclosures in that a polyvalent metal ion first complexes with an indicator to form a polyvalent metal ion-indicator complex having a first color. Then, as a result of contact between the polyvalent metal ion-indicator complex and a test sample including a sufficient concentration of cations, the cations compete with the polyvalent metal ion for the indicator and displace a number of the polyvalent metal ions from the polyvalent metal ion-indicator complex. The number of polyvalent metal ions displaced from the polyvalent metal ion-indicator complex is directly proportional to the concentration of cations in the test sample.

As polyvalent metal ions are displaced from the polyvalent metal ion-indicator complex, the polyvalent metal-ion indicator complex undergoes a color transition from a first color to a second color. The color transition can be correlated to the specific gravity of the test sample because the color transition is directly proportional to the number of polyvalent metal ions displaced from the polyvalent metal ion-indicator complex, which in turn is directly proportional to the cation concentration of the test sample. The cation concentration of the test sample is directly proportional to test sample specific gravity. Accordingly, and in contrast to the Falb et al. and Stiso et al. disclosures, the present method is essentially independent of test sample pH because the color transition results from a pH-independent displacement of polyvalent metal ions, such as mercuric ions, from a complex formed with an indicator, like diphenylcarbazone.

The present invention provides a composition and method for semiquantitatively determining the specific gravity of urine and other aqueous test samples by utilizing a reagent composition including a polyvalent metal ion and an indicator capable of forming a polyvalent metal ion-indicator complex. European Patent Application 0 349 934 discloses a test strip and method of determining specific gravity of a sample utilizing a composition including a buffer, a complex former and a pH indicator dye. The complex former can be a crown ether, a cryptand, a podand or a multifunctional ligand. The method disclosed in the European Application is pH dependent, and utilizes a standard pH indicator dye, such as bromothymol blue or thymol blue. European Patent Application 0 349 934 does not teach or suggest a combination of a polyvalent metal ion, an indicator and buffer, as utilized in the present invention, to provide an essentially pH independent assay for specific gravity.

In contrast to the above-described patents, and in contrast to the presently available commercial test strips, the method of the present invention provides a semiquantitative measurement of test sample specific gravity by utilizing a reagent composition including a polyvalent metal ion having a valence of at least two; an indicator capable of interacting with the polyvalent metal ion to provide a polyvalent metal ion-indicator complex having a first color; and a buffer wherein the method is essentially independent of test sample pH. The present reagent composition undergoes a sufficient color transition upon contact with a test sample to provide a semiquantitative specific gravity assay for liquids having a specific gravity of about 1.000 to about 1.035. Hence, new and unexpected results are achieved in the wet phase and the dry phase reagent strip assay of urine and other aqueous test samples for specific gravity.

SUMMARY OF THE INVENTION

In brief, the present invention is directed to a method and composition for semiquantitatively determining the specific gravity of an aqueous test sample, and especially the specific gravity of a biological fluid, such as urine, perspiration, or serum. The method utilizes a reagent composition capable of interacting with a test sample to produce a detectable and measurable response that can be correlated to the specific gravity of the test sample. The response is essentially independent of the pH of the test sample. For home use, the reagent composition produces a visually detectable response. For laboratory use, the reagent composition produces a response that is detectable visually or instrumentally.

The method is suitable for wet phase assays and for dry phase assays. In a dry phase assay, the reagent composition is incorporated into a carrier matrix to provide a test pad of a test device. The carrier matrix of the test pad comprises a bibulous porous material, like filter paper, or a nonbibulous porous material, like a glass fiber or a permeable layer of a polymeric material. The reagent composition is homogeneously incorporated into the carrier matrix, and the carrier matrix then holds the reagent composition homogeneously throughout the carrier matrix in a known concentration while maintaining carrier matrix penetrability for the liquid test sample.

More particularly, the present invention is directed to a method of semiquantitatively assaying for the specific gravity of urine and other biological or aqueous test samples by utilizing a new reagent composition. It has been demonstrated that a reagent composition including: 1) a polyvalent metal ion, 2) an indicator capable of interacting with the polyvalent metal ion to provide polyvalent metal ion-indicator complex having a first color, and 3) a buffer, affords sufficient sensitivity to test sample specific gravity, and a sufficient color differentiation between test samples of different specific gravity. In accordance with an important feature of the present invention, the specific gravity of urine and other aqueous test samples can be determined, semiquantitatively, between about 1.000 and about 1.035, and especially between about 1.005 and about 1.030.

The present method does not rely upon a pH change to provide the color transition and is essentially independent of test sample pH. However, a buffer is included in the reagent composition to achieve a sufficient color transition, and accordingly a more accurate measurement of the specific gravity of the test sample. The buffer is included in the reagent composition to maintain the reagent composition within the pH range wherein the polyvalent metal ion and indicator can interact to form a polyvalent metal ion-indicator complex having a first color.

Therefore, one aspect of the present invention is to provide a method and composition for semiquantitatively determining the specific gravity of an aqueous liquid. The new composition interacts with cations present in the aqueous test sample to produce a visible change, such as a change in color of a test device, that is indicative of the specific gravity of the test sample.

Another aspect of the present invention is to provide a method of assaying urine or other aqueous test samples, said method having sufficient sensitivity and sufficient visual color resolution to allow differentiation between, and the semiquantitative measurement of, test sample specific gravities.

Another aspect of the present invention is to provide a method of assaying urine or other aqueous test samples utilizing a reagent composition capable of interacting with cations present in urine or other aqueous test samples, and undergoing a detectable and measurable color transition, independent of test sample pH, to establish the specific gravity of the test sample.

Another aspect of the present invention is to provide a reagent composition that interacts with cations present in the test sample and undergoes a visually or instrumentally differentiable color transition to allow the determination of test sample specific gravity of about 1.000 to about 1.035, and especially about 1.005 to about 1.030.

Another aspect of the present invention is to provide a method of assaying for the specific gravity of a liquid test sample by incorporating a reagent composition into a dry phase detection device, wherein the reagent composition comprises: (a) a polyvalent metal ion having a valence of at least two, like mercuric ion or calcium ion; (b) an indicator capable of interacting with the polyvalent metal ion to provide a polyvalent metal ion-indicator complex having a first color; (c) a buffer; and (d) a suitable carrier.

Still another aspect of the present invention is to provide a new and improved method of assaying for the specific gravity of an aqueous test sample by utilizing a test device including a carrier matrix, said carrier matrix comprising a bibulous matrix, like filter paper, or a nonbibulous matrix, like a glass fiber or a layer of a permeable polymeric material, and said carrier matrix having incorporated therein a reagent composition capable of interacting with cations present in the test sample to provide a color transition.

A further aspect of the present invention is to provide an improved dry phase test strip that incorporates a reagent composition comprising a polyvalent metal ion, a suitable indicator and a buffer into the carrier matrix, and thereby provide a pH independent semiquantitative assay for the specific gravity of a test sample.

The above and other aspects and advantages and novel features of the present invention will become apparent from the following detailed description of the preferred embodiments.

DETAILED DESCRIPTION OF THE PREFERRED EMBODIMENTS

In accordance with the method of the present invention, the semiquantitative assay of aqueous test samples for specific gravity is accomplished by utilizing a reagent composition that includes a polyvalent metal ion; an indicator capable of interacting with the polyvalent metal ion to provide a polyvalent metal ion-indicator having a first color; and a buffer. By employing a reagent composition of the present invention, sufficient sensitivity and sufficient visual color differentiation between test samples of differing specific gravities is achieved. Surprisingly, the method does not rely upon a pH change to provide a color transition, and therefore the reagent composition can be buffered to a suitable pH range for maximum color transition.

The method and composition of the present invention is especially useful in urine assays. In accordance with the method and composition of the present invention, urine specific gravities between about 1.000 and about 1.035, and especially between 1.005 and 1.030, can be differentiated and measured semiquantitatively. Furthermore, the method and composition of the present invention also can be used to determine the specific gravity of blood plasma and serum; and more generally, the specific gravity of many other physiological fluids, like perspiration, as well.

Differentiating between specific gravities is clinically important because urine specific gravities that are either above or below the normal specific gravity range of about 1.010 to about 1.025 for a healthy individual may indicate a potential renal deficiency. A semiquantitative urine specific gravity assay interpreted in conjunction with assays for other urine analytes can assist in diagnosing a diseased state. It should be noted that in regard to urine specific gravities within the relatively normal range of about 1.010 to about 1.025, the method of the present invention still affords color differentiation and sensitivity to urine specific gravity. Clinical benefits are realized in this normal specific gravity range by interpreting the specific gravity assay in conjunction with urine assays for other analytes, such that all of the assays can provide information concerning an abnormal physiological state that must be investigated further.

To achieve the full advantage of the present invention, the method and composition are employed in dry phase, test pad assays to determine the specific gravity of urine or other aqueous test samples. A dry phase test strip, including a test pad comprising a carrier matrix incorporating a reagent composition of the present invention, allows the rapid semiquantitative assay of urine specific gravity by visual means. The method and composition of the present invention also are useful in wet phase assays.

In particular, the present invention allows determination of the specific gravity of a test sample by the visual color change of a test pad on a test strip or by the visual color change of an aqueous solution. Test sample specific gravity is determined by correlating the cation concentration of the test sample to test sample specific gravity. The test strip includes a test pad comprising an inert carrier matrix incorporating a reagent composition comprising a sufficient amount of a polyvalent metal ion; an indicator capable of interacting with the polyvalent metal ion to provide a polyvalent metal ion-indicator complex having a first color; and a buffer.

The present composition and method allow the rapid colorimetric determination of the specific gravity of a test sample. Previous specific gravity assay methods employed indicator dyes that are sensitive to solution pH. The present method is essentially independent of the pH normally encountered in urine samples, e.g., pH of about 3 to about 9.

The pH indicator dyes conventionally used in specific gravity assays undergo color transitions due to a pH change in the solution resulting from an ion exchange between a polyelectrolyte and cations present in the test sample. The phenomena is fully described in Falb et al. U.S. Pat. No. 4,318,709 and Stiso et al. U.S. Pat. No. 4,376,827, wherein the various dyes, the polyelectrolytes and the buffers required to observe the pH change are disclosed. The Falb et al. and Stiso et al. patents basically describe the present day dry phase test strips employed to assay for urine specific gravity. These present day test strips generally include: (a) an indicator dye that normally undergoes a color transition in the neutral pH range of about 6 to about 8, such as bromothymol blue; (b) a partially neutralized polyelectrolyte; and (c) a buffer.

In accordance with the methods of Stiso et al. and Falb et al., as the ionic strength of the urine increases, hydrogen ions are released into the solution due to an ion exchange between the cations in the test sample and the polyelectrolyte. The overall result is a drop in pH of the solution, and the bromothymol blue indicator changes color from blue-green to green to yellow-green in response to the pH change caused by increasing ionic strength. The increase in ionic strength of an aqueous test sample is directly related to an increase in specific gravity; the color transition of the dye therefore is empirically related to specific gravity values. The present day method suffers from the disadvantage of color transition instability, wherein the color transition fades over a time period of minutes. Accordingly, the accuracy of the results are technique dependent.

The methods disclosed by Stiso et al. and Falb et al. also are sensitive to normal fluctuations in test strip manufacturing. For example, variations in carrier materials and in drying conditions of the test strip, and lot-to-lot differences in a polyelectrolyte, each can influence the final surface pH of the test strip. Variances in the final surface pH of the test strip result in less accurate specific gravity measurements because the test strip becomes either more or less sensitive to pH changes.

In accordance with the present method, assays for the specific gravity of an aqueous test sample are determined by examining a solution or a dry phase test strip for a visual color change after the test sample contacts a solution or a test strip incorporating the reagent composition. The test strip comprises a test pad, said test pad including a carrier matrix incorporating a reagent composition comprising a polyvalent metal ion, a suitable indicator and a buffer. In contrast to previous methods which utilized pH sensitive dyes, the present method is essentially independent of normally encountered pH values and the reagent composition can be buffered to provide a pH range that yields the most spectacular color transition.

The present invention differs from the methods disclosed by Stiso et al. and Falb et al. in that the present method does not rely upon a pH change to provide a color transition. Furthermore, the reagent composition can be buffered to a pH that provides the most spectacular color transition. This pH independence eliminates the need for specific gravity corrections of urine samples having a high pH. The present pH independent method also avoids the above-described manufacturing problems associated with the present pH-dependent test strips.

In accordance with an important feature of the present invention, the cation concentration of urine can be correlated to urine specific gravity. Therefore, measuring urine cation concentration provides an indirect method of measuring urine specific gravity. Urine specific gravity is determined from the color transition resulting from displacing the polyvalent metal ion from the polyvalent metal ion-indicator complex. In the present method, a polyvalent metal ion, such as mercuric ion, first is complexed to an indicator to provide a polyvalent metal ion-indicator having a first color. Then, in the presence of urinary cations, a portion of the polyvalent metal ions are displaced from the indicator, and the indicator then interacts with urinary cations to form a cation-indicator complex having a second color. Accordingly, a detectable and measurable color transition results.

More particularly, the ability of a polyvalent metal ion and an indicator to interact and form a polyvalent metal ion-indicator complex having a first color is influenced by the cation concentration of a solution, with the ability of the polyvalent metal ion and the indicator to form a complex decreasing as cation concentration increases. The present method utilizes this property in a pH independent method and device to assay an aqueous test sample for specific gravity.

Cations in solution affect the ability of the polyvalent metal ion to complex with the indicator because the cations successfully compete with the polyvalent metal ion with regard to complexing with the indicator. Therefore, as the cation concentration of a solution increases (i.e., specific gravity increases), a greater portion of the polyvalent metal ions is displaced from the indicator because a fraction of the cations in solution preferentially complex with the indicator at the expense of the polyvalent metal ion. The displacement of polyvalent metal ions from the indicator into the solution results in a color transition from the first color of the polyvalent metal ion-indicator complex to a second color. Therefore, the amount of polyvalent metal ion displaced from the indicator, as determined by the color transition, can be correlated to the cation concentration of the test sample and, in turn, to test sample specific gravity.

The method of the present invention utilizes a color transition resulting from cations in the test sample displacing polyvalent metal ions complexed with an indicator. The reagent composition allows the semiquantitative specific gravity measurement of a test liquid having a specific gravity of about 1.000 to about 1.035. In accordance with an important feature of the present invention, the displacement of polyvalent metal ions from the polyvalent metal ion-indicator complex provides a differentiable color transition that can be correlated to the specific gravity of a test sample. Measurement of test sample specific gravity is achieved because a sufficient color resolution exists between test samples of different specific gravity.

Therefore, the reagent composition of the present invention comprises: (a) a polyvalent metal ion; (b) an indicator capable of interacting with the polyvalent metal ion to provide a polyvalent metal ion-indicator complex having a first color; (c) a buffer, and (d) a suitable carrier. The reagent composition is used in a method, such as in a wet phase method or in a dry phase test strip method, to semiquantitatively assay a test sample, like urine, for specific gravity.

The reagent composition includes a metal ion having a valence of at least two, i.e., a polyvalent metal ion. The polyvalent metal ion is present in an amount such that essentially all of the indicator is complexed with the polyvalent metal ion. An excess amount of polyvalent metal ion does not adversely affect the assay, but is wasted.

The particular amount of polyvalent metal ion included in the reagent composition can be determined by a person skilled in the art of designing test kits after considering the particular polyvalent metal ion and the particular indicator included in the reagent composition in order to provide a maximum color transition. Generally, however, the polyvalent metal ion is present in the reagent composition in an amount of about 0.5 mM to about 6 mM, and preferably about 1 mM to about 4 mM.

In accordance with an important feature of the present invention, it is envisioned that essentially any polyvalent metal ion: 1) capable of complexing with the indicator, and 2) providing a polyvalent metal ion-indicator complex that undergoes a color transition upon displacement of the polyvalent metal ion from the complex, can be included in the reagent composition of the present invention. Accordingly, a polyvalent metal ion useful in the reagent composition is, for example, but not limited to, ferric ion, ferrous ion, calcium ion, magnesium ion, cobalt(II) ion, cobalt(III) ion, cupric ion, mercuric ion, stannic ion, nickel(II) ion, lead(II) ion, manganese(III) ion, cadmium(II) ion, zinc(II) ion, molybdenum(V) ion, chromium(IV) ion and vanadium(III) ion, or mixtures thereof. To achieve the full advantage of the present invention, the polyvalent metal ion is mercuric ion, calcium ion, lead ion, or ferric ion.

In addition, other polyvalent metal ions also can be used as long as the polyvalent metal ion can be complexed to the indicator to provide a polyvalent metal ion-indicator having a first color. The polyvalent metal ion is included in the reagent composition in the form of a water soluble salt, wherein the anion does not interfere with the specific gravity assay. Typically, the polyvalent metal ion is included in the reagent composition as a metal chloride salt.

In addition to the polyvalent metal ion, the reagent composition also includes an indicator capable of interacting with the polyvalent metal ion to form a polyvalent metal ion-indicator complex having a first color. After the polyvalent metal ion is displaced from the polyvalent metal ion-indicator complex by cations present in the test sample, the reagent composition undergoes a color transition to a second color. The color transition can be either an increase or a decrease in color intensity and degree. The color transition usually is a decrease in color intensity and degree.

Therefore, a solution including a polyvalent metal ion complexed to an indicator undergoes a color change in the presence of cations because a portion of the polyvalent metal ions are displaced from the polyvalent metal ion-indicator complex. Monovalent cations, like sodium and potassium, are the predominant cations in test samples like urine. However, relatively high concentrations of divalent cations, like calcium and magnesium, also are present in urine. The monovalent and divalent cations displace polyvalent metal ions complexed with the indicator because the monovalent and divalent cations successfully compete with the polyvalent metal ions for the indicator.

In general, the indicator can be essentially any compound, such as a dye, that interacts with the polyvalent metal ion in the reagent composition to provide a polyvalent metal ion-indicator complex. Such indicators undergo a color transition in response to displacement of polyvalent metal ions from the polyvalent metal ion-indicator complex. The polyvalent metal ions are displaced from the indicator by cations, like sodium or magnesium, present in the test sample. The degree and intensity of the color transition are directly related to the concentration of monovalent and divalent cations in the test sample; and the concentration of the cations in the test sample is directly related to the specific gravity of the test sample. Therefore, the degree and intensity of the color transition are correlated to the specific gravity of the test sample.

The particular indicator included in the reagent composition can be determined by those skilled in the art of designing test kits after considering the particular polyvalent metal ion included in the reagent composition in order to provide a specific gravity assay having maximum visual color resolution and maximum sensitivity. The indicator generally is present in the reagent composition in a concentration of about 1 mM to about 10 mM, and preferably about mM to about 8 mM. To achieve the full advantage of the present invention, the indicator is present in the reagent composition at a concentration of about 3 mM to about 5 mM.

Several indicators useful in the method of the present invention are well known dyes that presently are available commercially. Many useful indicators have been used to colorimetrically detect polyvalent metal ions. For example, diphenylcarbazone has been used to assay for mercuric ions and diphenylthiocarbazone has been used to assay for lead ions. Eriochrome black T has been used to assay for calcium or magnesium ions. However, such indicators have not been used to assay a test sample for specific gravity.

Examples of indicators that bind to a polyvalent metal ion and provide a polyvalent metal ion-indicator complex having a first color include, but are not limited to, 1,10-phenanthroline, bathophenanthroline, 2,2'-dipyridine, tripyridyl-s-triazine, Tiron® (disodium pyrocatechol-3,5-disulfonate), dimethylglyoxime, rubeanic acid, eriochrome black T, rhodizonic acid, calmagite, gallocyanine, diphenylthiocarbazone, diphenylcarbazone, potassium ferricyanide, pyrocatechol violet, 5-methyl-1,10-phenanthroline, 5-nitro-1,10-phenanthroline, 3-(4-phenyl-2-pyridyl)-5,6-diphenyl-1,2,4-triazine, 3-(4-phenyl-2-pyridyl)-5,6-diphenyl-1,2,4-triazinetrisulfonic acid trisodium salt, 3-(2-pyridyl)-5,6-diphenyl-1,2,4-triazine, 3-(2-pyridyl)-5,6-diphenyl-1,2,4-triazinedisulfonic acid disodium salt, phenyl-2-pyridyl ketoxime, 4'-phenyl-2,2',2"-terpyridine, 2,2',2"-terpyridine, 4,4',4"-triphenyl- 2,2',2"-terpyridine, 2,3,5,6-tetrakis(2'-pyridyl)pyrazine, 2,2'-biquinoline, bis-cyclohexanone oxaldihydrazone, 2,4-bis(5,6-diphenyl 1,2,4-triazin-3-yl)pyridine, 2,4-bis(5,6-diphenyl-1,2,4-triazin-3-yl)pyridinetetrasulfonic acid tetrasodium salt, 4,4'-dihydroxy-2,2'-biquinoline, 4,7-dihydroxy-1,10-phenanthroline, 4,4'-dimethyl-2,2'-bipyridine, 2,9-dimethyl-1,10-phenanthroline, 2,9-dimethyl-4,7-diphenyl-1-10-phenanthroline, 2,9-dimethyl-4,7-diphenyl-1,10-phenanthrolinedisulfonic acid, 4,7-dimethyl-1,10-phenanthroline, 5,6-dimethyl-1,10-phenanthroline, 4,7-diphenyl 1,10-phenanthroline, and mixtures thereof.

Such indicators exhibit an excellent ability to bind to a polyvalent metal ion and provide a polyvalent metal ion-indicator complex having a first color. Other non-limiting exemplary indicators useful in the reagent composition can be found in the *Handbook of Chemistry and Physics.* 71st Edition (1990–1991) at pages 8-8 through 8-11, incorporated herein by reference.

The present method is performed in a pH range of about 4 to about 9. A specific pH range is selected wherein the indicator undergoes a maximum color change upon interaction with the polyvalent metal ion. The reagent composition, therefore, includes a buffer to maximize the color transition. The buffer maintains the reagent composition at a substantially constant pH to optimize formation of the polyvalent metal ion-indicator complex.

Any of various types of buffers can be used in the reagent composition of the present invention to provide a desired pH. The amount and type of buffer included in the reagent composition, and the buffer pH, depends upon the nature of the polyvalent metal ion and the indicator included in the reagent composition. The concentration of the buffer usually is about 20 millimolar (mM) to about 500 mM, and preferably about 50 mM to about 200 mM. The particular buffer used in the reagent composition also depends upon, and varies with, the indicator and polyvalent metal ion included in the reagent composition. For optimum assay results, the pH of the reagent composition generally is maintained at a pH value in the range of about 4 to about 9, and preferably in the range of about 5 to about 9. To achieve the full advantage of the present invention, the buffer maintains the pH value of the reagent composition at about 5 to about 8.

Exemplary buffers include, but are not limited to, acetate; BICINE; phthalate, borate; trichloracetate; sulfosalicylate; phosphate; tartarate; glycine; citrate; succinate; maleic acid; 2,2-bis(hydroxymethyl)-2,2',2"-nitrilotriethanol; 3,3-dimethylglutaric acid; 3-N-morpholinopropanesulfonic acid (MOPS); malonic acid; 1,3-bis[tris(hydroxymethyl)methylamino]propane (Bis-TRIS); tris(hydroxymethyl)aminomethane (TRIS); N-(carbamoylmethyl)taurine (ACES); tris(hydroxymethyl)aminomethane-maleic acid (TRIS-maleate); tris(-hydroxymethyl)aminomethane-malonic acid (TRIS-malonate); 3-N-(trishydroxymethyl)methylamino-2-hydroxypropanesulfonic acid (TAPSO); 2-([tris(hydroxymethyl)methyl]amino)ethanesulfonic acid (TES); 1,4-piperazinebis(ethanesulfonic acid) (PIPES); 4-morpholinoethanesulfonic acid (MES); N-2-hydroxyethylpiperazine-N'-2-ethanesulfonic acid (HEPES); and other suitable buffers well known in the art, or mixtures thereof.

In addition to the indicator, the polyvalent metal ion and the buffer, other optional ingredients that do not materially alter the nature or the function of the essential ingredients, and that do not interfere with the assay for specific gravity, also can be included in the reagent composition. For example, the reagent composition optionally can include a compound to improve the wetting of the test pad of the test device by the test sample. This compound usually is a nonionic surfactant. An octoxynol, a nonoxynol or an ethoxylated fatty alcohol is the preferred nonionic surfactant. The surfactant is included in the indicator reagent composition in a concentration of 0 mM to about 200 mM, and preferably in a concentration of 0 mM to about 100 mM.

The reagent composition also can include a polymeric material that improves the stability and uniformity of the color transition of the test device. Suitable polymeric materials include, but are not limited to, polyvinyl alcohol, gum arabic, gelatin, algin, carrageenan, casein, albumin, methyl cellulose and similar natural and synthetic polymeric materials. The reagent composition however is essentially free of polyelectrolytes because polyelectrolytes can interfere with the formation of the polyvalent metal ion. indicator complex and the color transition of the complex from a first color to a second color. The polymeric material generally is included in the reagent composition in an amount of 0% to about 5%, and preferably 0% to about 4%, by total weight of the reagent composition.

In addition, inert background dyes can be included in the reagent composition to improve the color resolution and differentiation of the color transition in the present assay for specific gravity. Suitable background dyes include, but are not limited to, ethyl orange (4-(4-diethylaminophenylazo) benzenesulfonic acid); Orange G (4-(2-hydroxy-(7,9 sodium disulfonate)-1-naphthylazo)-benzene); disperse orange 11, 13, or 25; calcomine orange; methyl orange; and orange II (4-(2-hydroxy-1-naphthylazo) benzenesulfonic acid), or combinations thereof. A background dye is included in the reagent composition of the present invention at a concentration of 0 mM to about 2 mM, and preferably 0 mM to about 1 mM.

The carrier for the ingredients included in the reagent composition is water; a water miscible alcohol or a water-alcohol mixture. Suitable water-miscible alcohols, include, for example, but are not limited to, methanol, ethanol, isopropyl alcohol and combinations thereof. However, because of the limited water or alcohol solubility of particular ingredients included in the indicator reagent composition, other organic solvents such as ethylene glycol, propylene glycol, acetone, dimethylformamide, dimethylsulfoxide, acetonitrile, ethyl acetate and similar solvents can be included, for used as in the carrier. The selection of a suitable organic solvent or solvents, in addition to water and alcohols, to include in the carrier of the reagent composition is within the capability of those skilled in the art of designing diagnostic assays. A carrier including an organic solvent, like methanol, ethanol or ethyl acetate, either with or without water, is especially preferred because a carrier matrix impregnated with the reagent composition can be dried within a few to several minutes.

As previously described, the reagent composition undergoes a color transition upon contact with a test sample to provide an assay for test sample specific gravity. The intensity and degree of the color transition are used to semiquantitatively determine the specific gravity of the test sample. In accordance with an important feature of the present invention, a reagent composition of the present invention provides a sufficiently resolved and differentiated color transition such that the specific gravity of a test sample can be measured without the use of color-measuring instruments, such as spectrophotometers or colorimeters. However, if desired, such color-measuring instruments can be used to measure the difference in color degree and intensity between the test sample and a solution having a known specific gravity.

The intensity and degree of the color transition are used to determine the specific gravity of the test sample by comparing or correlating the color produced by the test sample to colors produced by solutions having a known specific gravity. In accordance with an important feature of the present invention, the reagent composition provides a sufficiently resolved and differentiated color transition such that the specific gravity of the test sample can be measured for test samples having a specific gravity of about 1.000 to about 1.035 without the use of color-measuring instruments.

Accordingly, the specific gravity assay method of the present invention, utilizing a reagent composition including a polyvalent metal ion, an indicator capable of interacting with the metal ion to provide a polyvalent metal ion-indicator complex, and a buffer, afford a reliable semiquantitative specific gravity assay, and also increases physician confidence in the specific gravity assay. In addition, because of the large number of urine assays for specific gravity being performed at home by untrained individuals, as opposed to trained physicians or technicians in the laboratory, it is imperative to provide reliable assay methods for the specific gravity of urine and serum.

To demonstrate the new and unexpected results achieved by the method and composition of the present invention, reagent compositions, including a polyvalent metal ion, a suitable indicator and a buffer, were prepared, then used in wet phase assays and in dry phase assays for the specific gravity of a test sample.

EXAMPLE 1

Reagent Composition and Effects of Cations on the Reagent Composition

An aqueous reagent composition of the present invention including a polyvalent metal ion (mercuric ion; 2 mM) and an indicator (diphenylcarbazone; 4 mM) in deionized water, and buffered to pH 7.0 with Bis TRIS, was prepared. The reagent composition was intense purple in color. The reagent composition changed from intense purple to colorless in response to urinary concentrations of sodium, calcium or magnesium ions. The results show that urinary cations displace a portion of the polyvalent metal ions from the polyvalent metal ion-indicator complex, and that a color transition occurs.

In another experiment, the reagent composition of Example 1 was contacted with standardized solutions including the urinary cations sodium, potassium, calcium and magnesium, and having an increasing specific gravity of 1.000 to 1.030. The resulting color transitions of the wet phase assays ranged from intense purple through purple-lavender through lavender to pink-lavender as the specific gravity increased from 1.000 to 1.030.

In accordance with an important feature of the present invention, the color resolution achieved by using a present reagent composition, e.g., the reagent composition of Example 1, permits the detection and differentiation of test sample specific gravities in the range of about 1000 to about 1.035.

A reagent composition including a polyvalent metal ion, an indicator and a buffer, as described above in Example 1, can be used in dry phase, test pad assays for specific gravity. The dry phase, test pad assay for specific gravity utilizing the reagent composition is performed in accordance with methods well known in the art. In general, the assay for specific gravity is performed by contacting the urine or other test sample with an analyte detection device that includes the reagent composition. The analyte detection device can be dipped into the test sample, or the test sample can be applied to the analyte detection device dropwise. The resulting change in color of the analyte detection device reveals the specific gravity of the test sample; and, if so designed, the resulting color transition can be compared to a standardized color chart to provide a measurement of the specific gravity of the urine or test sample.

Typically, the analyte detection device is a test strip impregnated with a reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the test ample to move, in response to capillary forces, through the matrix to contact the reagent composition and produce a detectable and measurable color transition.

The carrier matrix can be any substance capable of incorporating the chemical reagents required to perform the assay of interest, as long as the carrier matrix is substantially inert with respect to the chemical reagents and does not contaminate the urine or other test samples either by test sample extraction of components comprising the carrier matrix or by appreciably altering the urine or test sample in a way to make the subsequent assays inconclusive, inaccurate or doubtful. The carrier matrix also is porous or absorbent relative to the liquid test sample.

The expression "carrier matrix" refers either to bibulous or nonbibulous matrices that are insoluble in water and other physiological fluids and that maintain their structural integrity when exposed to water and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally-occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate or polystyrene, and the carrier matrix is most advantageously constructed from filter paper or polymeric films.

To achieve the full advantage of the present invention, the reagent composition is incorporated into a suitable carrier matrix to provide a test pad, and the test pad is utilized in a dry phase test strip for the specific gravity assay of an aqueous test sample. The method of the present invention provides an economical, accurate and reliable assay of aqueous test samples that can be performed at home or in the laboratory.

In accordance with the method of the present invention, to perform a dry phase, test strip assay for specific gravity, the reagent composition including a polyvalent metal ion, an indicator, a buffer and a carrier first is prepared. A bibulous matrix, such as filter paper, like WHATMAN CCP500 filter paper, available commercially from Whatman Ltd., Maidstone, Kent, U.K., then is saturated with the reagent composition either by spreading, by immersing or by spraying the reagent composition onto precut strips of the filter paper. After removing the carrier by oven drying in an air oven at about 50° C. for about 15 to 20 minutes, the filter paper incorporating the reagent composition is cut to an appropriate size, such as a pad having dimensions of about 0.25 cm by about 0.25 cm to about 1.0 cm by about 1.0 cm. The filter paper incorporating the reagent composition then is secured to an opaque or transparent hydrophobic plastic handle with double sided adhesive tape.

The resulting test strip then was dipped into a fresh, uncentrifuged urine sample for a sufficient time to saturate the test pad with the sample. After waiting a predetermined time, such as about 15 seconds to about 60 seconds, the test strip is examined, either visually or instrumentally, for a response. The degree and intensity of the color transition of the test pad reveal the specific gravity of the urine sample.

In accordance with another important feature of the present invention, it is well within the experimental techniques of those skilled in the art of preparing test devices to determine the proper balance between size of test pad; the strength of reagent composition; the identity and amount of the polyvalent metal ion, the indicator and the buffer in the reagent composition; the amount of test sample; and the method of introducing the test sample to the test strip, such as by pipetting rather than dipping, to provide detectable and differentiable color transitions, such that a comparison, either visually or instrumentally, to color standards derived from solutions of known specific gravity is possible.

In many cases simple visual observation of the test strip provides the desired information. If more accurate information is required, a color chart bearing color spots corresponding to various standard specific gravities can be prepared for the particular reagent composition used in the test strip. The resulting color of the test strip after contact with the urine sample then can be compared with the color spots on the chart to determine the specific gravity of the test sample.

If a still more accurate determination is required, a spectrophotometer or colorimeter can be used to more precisely determine the degree and intensity of the color transition. In addition, the dry phase, reagent strip assay can be made quantitative by employing spectrophotometric or colorimetric techniques, as opposed to visual techniques, in order to more reliably and more accurately measure the degree and intensity of the color transition, and therefore more accurately measure the specific gravity of the test sample.

In accordance with an important feature of the present invention, the reagent composition includes a polyvalent metal ion and an indicator that are capable of interacting to form a complex having a first color. In the presence of a sufficient amount of cations, the polyvalent metal ion is displaced from the complex to provide a color transition. The color transition can be from a first color (i.e., the color of the polyvalent metal ion-indicator complex) to a second color, from a color to colorless, or from colorless to a color, as long as the color transition is sufficient for detection and differentiation.

Usually, the polyvalent metal ion and the indicator form a complex most efficiently within a particular, and relatively narrow, pH range. Therefore, the reagent composition is buffered within the pH range wherein complex formation is favored. To achieve the full advantage of the present invention, the reagent composition is buffered to a pH of about 4 to about 9. Within this pH range, the color transition is most spectacular and assay errors due to urine pH are essentially eliminated.

The following Table I illustrates various combinations of polyvalent metal ions and indicators at various pH values, and the color transition resulting from displacing the polyvalent metal ion from the polyvalent metal ion-indicator complex. The color transitions illustrated in Table I are sufficiently differentiable to provide a method of measuring test sample specific gravity.

TABLE I

COLOR TRANSITIONS RESULTING FROM AN INTERACTION BETWEEN A POLYVALENT METAL ION AND AN INDICATOR

| METAL ION | INDICATOR | pH | COLOR TRANSITION[1] |
|---|---|---|---|
| FERROUS[2] | 1,10-PHENANTHROLINE[3] | 5.0–9.0[4] | MOD. ORANGE |
| | BATHOPHENANTHROLINE | 5.0–9.0 | BRIGHT PINK |
| | POTASSIUM FERRICYANIDE | 5.0–6.0 | MOD. BLUE |
| | 2,2'-DIPYRIDYL | 5.0–9.0 | MOD. PINK |
| | TRIPYRIDYL-S-TRIAZINE | 5.0–8.0 | INT. PURPLE |
| FERRIC | TIRON | 5.0 | MOD. BLUE |
| | POTASSIUM FERROCYANIDE | 5.0–7.0, 9.0 | MOD. PURPLE |
| | PYROCATECHOL VIOLET | 5.0 | PURPLE TO ORANGE |
| NICKEL | DIMETHYLGLYOXIME | 8.0 | FAINT PINK |
| | RUBEANIC ACID | 8.0 | MOD. BLUE |
| CALCIUM | ERIOCHROME BLACK T | 1N NaOH | PURPLE TO RED ROSE |
| | SODIUM RHODIZONATE | 1N NaOH | PURPLE |
| MAGNESIUM | ERIOCHROME BLACK T | 8.0, 9.0 | PURPLE TO BLUE |
| | CALMAGITE | 9.0 | LAVENDER-RED TO BLUE |
| COBALTOUS | RUBEANIC ACID | 8.0 | MOD.-INT. YELLOW |
| | GALLOCYANINE | 8.0 | LAVENDER TO BLUE |
| LEAD | GALLOCYANINE | 6.0–8.0 | LAVENDER TO BLUE |
| | DITHIZONE | 5.0–9.0 | PINK-ORANGE TO YELLOW |
| | DIPHENYL- | 7.0–8.0 | MOD.-INT. |

TABLE I-continued
COLOR TRANSITIONS RESULTING FROM AN INTERACTION BETWEEN A POLYVALENT METAL ION AND AN INDICATOR

| Ex. 4 | METAL ION | INDICATOR | pH | COLOR TRANSITION[1] |
|---|---|---|---|---|
| | MERCURIC | CARBAZONE DIPHENYL-CARBAZONE | 4.0-8.0 | LAVENDER INT. PURPLE |

[1] Unless Otherwise indicated, the color change was from the listed color to essentially colorless, MOD. is moderate, INT. is intense; and
[2] Polyvalent metal ions were present at a concentration of 0.5 mM;
[3] Indicators were present at a concentration of 1.0 mM; and
[4] Combinations were tested at each pH, pH is buffered using the following buffers (0.5 M):
pH
4.0 Biphthalate
5.0 Acetate
6.0 MES
7.0 ACES
8.0 HEPES
9.0 Glycine.

Various combinations of a polyvalent metal ion, an indicator and a buffer also were tested to determine the response of a reagent composition to sodium, calcium and magnesium ions. In particular, aqueous solutions including either sodium ions (340 meq/L, milliequivalents per liter), calcium ions (10 meq/L) or magnesium ions (16 meq/L) were added to various buffered combinations of an indicator and a polyvalent metal ion. The results are summarized below in Table II. Table II illustrates that a reagent composition including mercuric ions and diphenylcarbazone provided an excellent response to sodium, calcium and magnesium ions in wet phase assays. Table II also illustrates that a reagent composition including calcium ions and eriochrome black T, or including lead ion and diphenylcarbazone, provided an excellent response to magnesium ions in wet phase assays. Accordingly, the judicious selection of a polyvalent metal ion and an indicator provides a reagent composition useful in a method to assay for test sample specific gravity.

TABLE II
REAGENT COMPOSITION RESPONSES TO SODIUM, CALCIUM AND MAGNESIUM IONS

| POLYVALENT METAL ION | INDICATOR | pH | RESPONSE | | |
|---|---|---|---|---|---|
| | | | Na | Ca | Mg |
| Mercuric | DPC[1] | 5.0 | Strong | Mod. | Faint |
| Ferrous | TPTZ | 8.0 | (none) | (none) | (none) |
| Ferric | TIRON | 5.0 | (none) | (none) | (none) |
| Ferrous | BATHO | 5.0-7.0 | (none) | (none) | (none) |
| Lead | GALLO | 6.0-8.0 | (none) | (none) | (none) |
| Lead | DITH | 9.0 | (none) | (none) | (none) |
| Lead | DPC | 7.0 | (none) | (none) | STRONG |
| | | 8.0 | (none) | (none) | (none) |
| Cobaltous | GALLO | 8.0 | (none) | (none) | (none) |
| Cupric | DPC | 6.0-8.0 | (none) | (none) | (none) |
| Calcium | ERIO BL T | 1N NaOH | (none) | (none) | STRONG |
| Calcium | RHOD | 1N NaOH | (none) | (none) | (none) |
| Nickel | RUBEANIC ACID | 8.0 | (none) | (none) | (none) |

[1] Abbreiations:
BATHO.: Bathophenanthroline
GALLO.: Gallocyanine
DITH.: Diphenylthiocarbazone
DPC: Diphenylcarbazone
ERIO BL T: Eriochrome Black T
RHOD.: Sodium Rhodizonate To show the new and unexpected results achieved by using a reagent composition of the present invention in a method of determining the specific gravity of a test sample, color space plots were prepared from assays using dry phase test strips comprising a test pad incorporating a reagent composition of the present invention into a filter paper matrix. The color space plots were obtained by contacting standardized solutions of known specific gravity with the dry phase test strips including the present reagent composition incorporated into a filter paper carrier matrix. In general, a color space plot includes three axes, the $L^*$, $A^*$ and $B^*$ axes. The values of $L^*$ plotted on the vertical axis are a measure of the intensity of color, whereby a large $L^*$ value denotes a light color and $L^*=0$ denotes a completely black color. The horizontal $A^*$ axis is a measure of the color transition from green to red, whereby the more positive the $A^*$ value, the more red the color, and analogously, the more negative the $A^*$ value, the more green the color. Similarly, the third axis, $B^*$, is a measure of the color transition from blue to yellow, whereby the greater the value of $B^*$, the more yellow the color, and analogously the smaller the value of $B^*$, the more blue the color.

The color space difference ($\Delta E$) is calculated from the following equation (Eq. 2):

$$\Delta E = \sqrt{(L_1^* - L_2^*)^2 + (A_1^* - A_2^*)^2 + (B_1^* - B_2^*)^2} \quad \text{Eq. 2}$$

wherein $L_1^*$, $A_1^*$, and $B_1^*$ are the color space values determined for a first standardized solution of known specific gravity;

$L_2^*$, $A_2^*$ and $B_2^*$ are the color space values determined for a second standardized solution of known specific gravity having a different specific gravity from the first standardized solution; and $\Delta E$ is the color space difference between the color space plots of the first and second standardized solutions.

The color space difference ($\Delta E$) is the straight line distance between two points in a three-dimensional color space plot. Theoretically, a color space difference of one (1) unit is the smallest color space difference the human eye can distinguish. However, because of the inherent differences between the visual capabilities of individuals, a color space difference ($\Delta E$) of about 3 units is required in order to practically and confidently distinguish between colors.

The $L^*$, $A^*$ and $B^*$ values plotted on the color space plots are calculated from the different reflectance measurements taken at sixteen different wavelengths evenly spaced between 400 nm (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values, X, Y and Z. $L^*$, $A^*$ and $B^*$ are calculated from the X, Y and Z tristimulus values using the following equations:

$$L^* = 116 \times [(Y/Y_0)^{\frac{1}{3}} - 16] \quad \text{(Eq. 3)}$$

$$A^* = 500 \times [(X/X_0)^{\frac{1}{3}} - (Y/Y_0)^{\frac{1}{3}}] \quad \text{(Eq. 4)}$$

$$B^* = 200 \times [(Y/Y_0)^{\frac{1}{3}} - (Z/Z_0)^{\frac{1}{3}}] \quad \text{(Eq. 5)}$$

wherein:

$X_o$, $Y_o$ and $Z_o$ are the tristimulus values for perfect white (i.e., reflectance=100% at all wavelengths), and X, Y and Z are the tristimulus values calculated as described above from the sixteen wavelengths between 400 nm and 700 nm.

From the color space plots, the color space differences (ΔE) were calculated, and are summarized and discussed in more detail hereinafter. In interpreting the data to be presented, a term such as ΔE (1.007–1.016) is the color space difference between specific gravity assays for standardized urine solutions having a specific gravity of 1.007 and 1.016. Similarly, the term ΔE (0–5) is the color space difference between assays of standardized solutions having a cation concentration of 0 mM and 5 mM respectively. The terms ΔE (0–8) and ΔE (0–340) are analogously defined.

To demonstrate the unexpected results provided by the present invention, a reagent composition was prepared, then utilized in assays for specific gravity. The results are set forth in Examples 2 through 4 and in Table III. The following Examples illustrate dry phase specific gravity assays utilizing a reagent composition of the present invention.

EXAMPLES 2 THROUGH 4

Dry Phase Test Strip Incorporating a Reagent Composition Including a Polyvalent Metaion Ion and an Indicator Dry phase test strips were prepared by first dipping Whatman CCP 500 filter paper either into a biphthalate buffer (50 mM) having a pH of 5 (Example 2) or a pH of 4 (Example 3). The test strips of Example 4 did not include a buffer. The buffered test strips of Examples 2 and 3 then were dried in a 70° C. oven for about 15 minutes. The test strips of Examples 2 through 4 next were dipped into an ethyl acetate solution that was 2 mM in mercuric chloride and 4 mM in diphenylcarbazone. The resulting test strips of Examples 2 through 4 then were dried for 3 minutes in a 70° C. oven. The test strips of Examples 2 through 4 were purple in color after drying. Individual test strips of Examples 2 through 4 retained a purple color after immersion into distilled water. The test strips responded to standardized solutions of urinary cations, and to urine samples, by changing to a lavender color.

In addition, individual test strips were dipped into standardized sodium chloride (340 mM), calcium chloride (5 mM) and magnesium chloride (8 mM) solutions, and into standardized urine solutions having a specific gravity of 1.000 to 1.023. The standardized urine solutions had the following properties:

|  | LOW | MEDIUM | HIGH |
|---|---|---|---|
| Specific Gravity | 1.007 | 1.016 | 1.023 |
| Sodium, meq/L | 44 | 135 | 130 |
| Calcium, meq/L | 2.6 | 7.8 | 11.0 |
| Magnesium, meq/L | 1.4 | 4.2 | 10.8 |
| Phosphate, mM | 11.2 | 14.6 | 20.3 |

The resulting color transition of each test strip was determined and converted into ΔE units by standard procedures known in the art. The ΔE units for these above-described experiments are summarized in TABLE III.

TABLE III

ΔE DIFFERENCES FOR TEST STRIPS INCORPORATING A REAGENT COMPOSITION OF THE PRESENT INVENTION

| Test sample | | | ΔE Values Ex. 2 | Ex. 3 | |
|---|---|---|---|---|---|
| Sodium Chloride (340 mM) vs. water | ΔE (0–340) | = | 33 | 32 | 25 |
| Calcium Chloride (5 mM) vs. water | ΔE (0–5) | = | 11 | 17 | 24 |
| Magnesium Chloride (8 mM) vs. water | ΔE (0–8) | = | 13 | 21 | 23 |
| Urine Specific Gravity | ΔE (1.000–1.007) | = | 16 | 22 | 11 |
| | ΔE (1.007–1.016) | = | 8 | 6 | 16 |
| | ΔE (1.016–1.023) | = | 3 | 2 | 6 |

In accordance with the method and composition of the present invention, the data presented in TABLE III illustrate that a reagent composition including a polyvalent metal ion and an indicator provide a dry phase assay for specific gravity wherein the color space differences generally are at, or above, the minimum human detectable limit of approximately three ΔE units. Generally, the color space difference values are at or above 3, therefore a color change is discernible by the human eye, and the assayer easily can differentiate between urine samples having specific gravities differing by as little as 0.006 in the specific gravity range of about 1.000 to about 1.023, and up to 1.050.

Specifically, the test strips showed an excellent sensitivity to sodium ions in the range of 0 mM to 340 mM that is readily perceptible to the human eye (ΔE of 25 to 33). The test strips also showed a sensitivity to calcium ions in the range of 0 mM to 5 mM (ΔE of 11 to 24) that is easily perceptible to the human eye, thereby allowing an assayer to distinguish between test samples including 0 mM or 5 mM calcium ions. Similarly, an assayer could easily discern between a solution that is 0 mM and 8 mM in magnesium ions (ΔE of 13 to 23). Overall, the results illustrated in Table IV show that the reagent composition has a sufficient sensitivity with respect to cation concentration to assay for specific gravity because specific gravity can be correlated to cation concentration.

The test strips also showed an excellent sensitivity to different urine specific gravities over the specific gravity range of 1.000 to 1.023. Except for one experiment, the ΔE value exceeded the minimal visually detectable limit. An assayer can detect and measure a urine specific gravity because the color space differences exhibited at or above the minimum detectable level of 3 color space units. Only the test strip incorporating the composition of Example 3, buffered to pH 4, had difficulty differentiating a medium specific gravity urine from a high specific gravity urine.

The reagent compositions of Examples 2 and 3 were buffered to pH 5 and 4, respectively. Test strips incorporating the reagent compositions of Examples 2 and 3 responded essentially identically to sodium chloride (340 mM) and to the medium and high specific gravity urine samples. Test strips incorporating the composition of Example 3 (pH 4) demonstrated a better response to calcium ions, magnesium ions and low specific gravity urine. These results were observed both visually and instrumentally.

The results obtained from test strips incorporating an unbuffered reagent composition (Example 4) also show an excellent response to urinary cations and to standardized urine samples. Test strips incorporating the composition of Example 4 demonstrate an improved response to magnesium and calcium ions, but a decreased response to sodium ions. It has been theorized that the biphthalate buffer included in Examples 2 and 3 complexed with the calcium and magnesium ions, and therefore test strips including the composition of Examples 2 and 3 demonstrated a decreased response to calcium and magnesium ions. Therefore, incorporating a buffer that cannot complex with magnesium and calcium ions is expected to improve test strip response to magnesium and calcium ions.

Test strips incorporating the composition of Example 4 demonstrated a decreased sensitivity to low specific gravity urine compared to test strips incorporating the compositions of Examples 2 and 3. However, the medium and high specific gravity urines are more readily discernible utilizing the composition of Example 4. Visual observations support this finding. The data illustrated in Table III show that a reagent composition of the present invention is sufficiently sensitive to urinary cations to assay a urine sample for specific gravity.

In another experiment, test strips were prepared that incorporated a reagent composition comprising either lead as the polyvalent metal ion and diphenylcarbazone as the indicator (Example 5), or calcium as the polyvalent metal ion and eriochrome black T as the indicator (Example 6). Test strips were

EXAMPLE 5

| Lead-Diphenylcarbazone | |
| --- | --- |
| Bis TRIS Buffer, 0.5M, pH 7.0. | 2 parts (by volume) |
| Lead Chloride, 1 mM | 1 part |
| Diphenylcarbazone, 1 mM | 1 part |

EXAMPLE 6

| Calcium-Eriochrome Black T | |
| --- | --- |
| Calcium chloride, 1 mM | 1 part (by volume) |
| Eriochrome Black T, 1 mM in 1N NaOH | 1 part |
| Distilled Water | 2 parts | prepared by dipping Whatman CCP 500 filter paper into the composition of either Example 5 or Example 6, then drying the resulting test strip.

After dipping a test strip incorporating the composition of either Example 5 or Example 6 into water, no response was observed (i.e., the test strips retained a blue color). Similarly, individual test strips incorporating either the composition of Example 5 or the composition of Example 6 that were dipped into an aqueous sodium chloride solution (340 mM) or an aqueous calcium chloride solution (5 mM) provided no response. However, test strips incorporating either the composition of Example 5 or of Example 6, and dipped into a magnesium chloride solution (8 mM), responded by changing to a red color. A concentration of 8 mM magnesium ions is an expected magnesium ion concentration in urine. Therefore, since magnesium ion concentration in urine correlates well with urine specific gravity, a reagent composition including lead and diphenylcarbazone, or calcium and eriochrome black T, can be used in a method to assay a urine sample for specific gravity.

A reagent composition including a polyvalent metal ion and a suitable indicator differentiates and measures the specific gravity of a test sample, allowing the semiquantitative specific gravity assay of test samples. The present reagent compositions provide an important and useful benefit of providing a specific gravity assay that relies upon the color transition of a polyvalent metal ion-indicator complex, as opposed to relying upon a pH change. Therefore, because the method is essentially independent of pH, the reagent composition is buffered to preclude assay inaccuracies due to urine pH and to maximize the color transition. As illustrated above, the polyvalent metal ion. indicator complex formed by the present reagent composition responds colorimetrically to the cation concentration of the test sample and provides a semiquantitative specific gravity assay.

It should be understood that those skilled in the art of designing test kits are able to design an optimal test strip incorporating a sufficient amount of a particularly effective reagent composition to permit the differentiation and measurement of test sample specific gravities differing by as little as 0.006 because an assay utilizing the method and composition of the present invention generally exhibit a color space difference of at least 3 units. This $\Delta E$ value is sufficient for detection by the human eye, and is easily detected by present day colorimeters or spectrophotometers. Similarly, the method and composition of the present invention provide an accurate specific gravity assay regardless of varying amounts of nonionic components, such as glucose or albumin, found in the test sample, as long as a sufficient number of cations are present in the test sample to cause a color transition that can be correlated to test sample specific gravity.

In accordance with another important feature of the present invention, full color development of a test strip incorporating a present reagent composition occurs within about 15 seconds to about 60 seconds after contacting the test strip with the test sample. Maximum color development occurs after about 30 seconds of contact. However, acceptable and trustworthy specific gravity assay results are achieved when the test strip is examined for a color change about 15 seconds after contact with the test sample. Such a short time for full color development of the test strip is an additional advantage of the reagent composition of the present invention. In addition, the color transition is sufficiently stable such that an accurate assay results from examining the test strip up to 60 minutes after contacting the test sample. Therefore, test strips incorporating the reagent composition of the present invention can be used to obtain fast and accurate specific gravity assays.

Overall, the present reagent composition incorporated into a suitable carrier matrix, such as filter paper, improves color differentiation between test samples having specific gravities differing by as little as 0.006 for test samples having a specific gravity of about 1.000 to about 1.035, and therefore provides excellent sensitivity to the specific gravity of aqueous test samples. In addition to excellent sensitivity, the method and composition of the present invention provide full color development and accurate assay results in a relatively short time.

Therefore, in accordance with an important feature of the present invention, accurate and reliable semiquantitative assays for the specific gravity of urine and other liquid test samples can be performed by utilizing a reagent composition comprising a polyvalent metal ion and a suitable indicator. The reagent composition provides sufficient color differentiation between test samples having different specific gravities, and is essentially independent of pH, thereby improving assay sensitivity.

Obviously, many modifications and variations of the invention as hereinbefore set forth can be made without departing from the spirit and scope thereof and therefore only such limitations should be imposed as are indicated by the appended claims.

What is claimed is:

1. A composition capable of exhibiting a detectable and measurable color transition in response to the metal cation concentration on an aqueous test sample, said composition consisting essentially of
   (a) a polyvalent metal ion;
   (b) an indicator capable of interacting with the polyvalent metal ion to provide a polyvalent metal ion-indicator complex having a first color;
   (c) a buffer; and
   (d) a carrier comprising water, a water miscible alcohol, or a mixture thereof, wherein the composition is essentially free of polyelectrolytes; and wherein the polyvalent metal ion-indicator complex undergoes a color transition from the first color to a second color in response to the metal cation concentration of the aqueous test sample, wherein the color transition is independent of a change in pH and is essentially independent of test sample pH.

2. The composition of claim 1 wherein the polyvalent metal ion is present in a concentration of about 0.05 to about 6 millimoles per liter of the composition.

3. The composition of claim 1 wherein the polyvalent metal ion is selected from the group consisting of ferric ion, ferrous ion, calcium ion, magnesium ion, cobalt(II) ion, cobalt(III) ion, cupric ion, mercuric ion, stannic ion, nickel(II) ion, lead(II) ion, manganese(III) ion, cadmium(II) ion, zinc(II) ion, molybdenum(V) ion, chromium(IV) ion, vanadium(III) ion, and mixtures thereof.

4. The composition of claim 1 wherein the indicator is present in a concentration of about 1 to about 10 millimoles per liter of the composition.

5. The composition of claim 1 wherein the indicator is selected from the group consisting of 1,10-phenanthroline, bathophenanthroline, 2,2'-dipyridyl, tripyridyl-s-triazine, disodium pyrocatechol-3,5-disulfonate, dimethylglyoxime, rubeanic acid, eriochrome black T, rhodizonic acid, calmagite, gallocyanine, diphenylthiocarbazone, diphenylcarbazone, potassium ferricyanide, pyrocatechol violet, 5-methyl-1,10-phenanthroline, 5-nitro-1,10-phenanthroline, 3-(4-phenyl-2-pyridyl)-5,6-diphenyl-1,2,4-triazine, 3-(4-phenyl-2-pyridyl)-5,6-diphenyl-1,2,4-triazinetrisulfonic acid trisodium salt, 3-(2-pyridyl)-5,6-diphenyl-1,2,4-triazine, 3-(2-pyridyl)-5,6-diphenyl-1,2,4 triazinedisulfonic acid disodium salt, phenyl-2-pyridyl ketoxime, 4,-phenyl-2,2'2''-terpyridine, 2,2',2''-terpyridine, 4,4',4''-triphenyl-2,2',2''-terpyridine, 2,3,5,6-tetrakis(2'-pyridyl)pyrazine, 2,2'-biquinoline, bis-cyclohexanone oxaldihydrazone, 2,4-bis(5,6-diphenyl-1,2,4-triazin-3-yl)pyridine, 2,4-bis(5,6-diphenyl-1,2,4-triazin-3-yl)pyridinetetra-sulfonic acid tetrasodium salt, 4,4'-dihydroxy-2,2'-biquinoline, 4,7-dihydroxy-1,10-phenanthroline, 4,4'-dimethyl-2,2'-bipyridine, 2,9-dimethyl-1,10-phenanthroline, 2,9-dimethyl-4,7-diphenyl-1-10-phenanthroline, 2,9-dimethyl-4,7-diphenyl-1,10-phenanthrolinedisulfonic acid, 4,7-dimethyl-1,10-phenanthroline, 5,6-dimethyl-1,10-phenanthroline and mixtures thereof.

6. The composition of claim 1 wherein the buffer is present in a concentration of about 20 to about 500 millimoles per liter of a buffer.

7. The composition of claim 1 wherein the composition is buffered to a pH of about 4 to about 9.

8. The composition of claim 1, wherein the buffer is selected from the group consisting of acetate; BICINE; phthalate; borate; trichloracetate; sulfosalicylate; phosphate; tartarate; glycine; citrate; succinate; maleic acid; 2,2-bis(hydroxymethyl)-2,2',2''-nitrilotriethanol; 3,3-dimethylglutaric acid; 3-N-morpholinopropanesulfonic acid; malonic acid; 1,3-bis[tris(hydroxymethyl)methylamino]propane; tris(hydroxymethyl)aminomethane; N-(carbamoylmethyl)taurine; tris(hydroxymethyl)aminomethane-maleic acid; tris(hydroxymethyl)aminomethane-malonic acid; 3-N-(trishydroxymethyl)-methylamino-2-hydroxypropanesulfonic acid; 2-([tris(hydroxymethyl)methyl]amino)-ethanesulfonic acid; 1,4-piperazinebis(ethanesulfonic acid); 4-morpholinoethanesulfonic acid; N-2-hydroxyethylpiperazine-N'-2-ethanesulfonic acid; and mixtures thereof.

9. The composition of claim 1 wherein the carrier further comprises 0% to about 20% by weight of the carrier of an organic solvent.

10. The composition of claim 1 wherein the polyvalent metal ion is selected from the group consisting of lead ion, ferric ion, mercuric ion, cobaltous ion, nickel ion, cupric ion, ferrous ion, calcium ion, magnesium ion, and mixtures thereof; and the indicator is selected from the group consisting of calmagite, rubeanic acid, dithizone, diphenylcarbazone, potassium ferricyanide, diphenylthiocarbazone, gallocyanine, eriochrome black T, 2,2'-dipyridyl, tripyridyl-s-triazine, rhodizonic acid, pyrocatechol violet, 1,10-phenanthroline, bathophenanthroline, disodium pyrocatechol-3,5-disulfonate, dimethylglyoxime, and mixtures thereof.

11. A composition capable of exhibiting a detectable and measurable color transition in response to the metal cation concentration of an aqueous test sample, said composition consisting essentially of:
   (a) a polyvalent metal ion-indicator complex comprising:
      (i) a polyvalent metal ion, and
      (ii) an indicator capable of interacting with the polyvalent metal ion to provide the polyvalent metal ion-indicator complex having a first color, wherein the polyvalent metal is present in a sufficient amount to complex essentially all of the indicator;
   (b) a buffer; and
   (c) a carrier comprising water, a water miscible alcohol, or a mixture thereof, wherein the composition is essentially free of polyelectrolytes; and wherein the polyvalent metal ion-indicator complex undergoes a color transition from the first color to a second color in response to the metal cation concentration of the aqueous test sample, wherein the color transition is independent of a change in pH and is essentially independent of test sample pH.

12. The composition of claim 11 wherein the indicator is present in a concentration of about 1 to about 10 millimoles per liter of the composition.

13. A method of determining the specific gravity of an aqueous test sample comprising:
   (a) contacting the aqueous test sample with a reagent composition consisting essentially of:
      (i) a polyvalent metal ion;

(ii) an indicator capable of interacting with the polyvalent metal ion to provide a polyvalent metal ion-indicator complex having a first color;
(iii) a buffer; and
(iv) a carrier comprising water, a water miscible alcohol or a mixture thereof, wherein the composition is essentially free of polyelectrolytes; and (b) determining the specific gravity of the aqueous test sample from the intensity and degree of a color transition of the polyvalent metal ion-indicator complex from the first color to a second color in response to the metal cation concentration to the aqueous test sample, wherein the color transition is independent of a change in pH and is essentially independent of test sample pH.

14. The method of claim 13 wherein the aqueous test sample is a biological fluid.

15. The method of claim 14 wherein the biological fluid is selected from the group consisting of urine, blood plasma, blood serum, and perspiration.

16. The method of claim 13 wherein the aqueous test sample has a specific gravity of about 1.000 to about 1.035.

17. The method of claim 13 wherein the intensity and degree of the color transition is determined visually or instrumentally.

18. A method of determining the specific gravity of an aqueous test sample comprising:
(a) contacting the aqueous test sample with a reagent composition consisting essentially of:
(i) a polyvalent metal ion-indicator complex having a first color, said polyvalent metal ion-indicator complex comprising:
(A) a polyvalent metal ion, and
(B) an indicator capable of interacting with the polyvalent metal ion to provide the polyvalent metal ion-indicator complex;
(ii) a buffer; and
(iii) a carrier comprising water, a water miscible alcohol, or a mixture thereof, wherein the composition is essentially free of polyelectrolytes; and
(b) determining the specific gravity of the aqueous test sample from the intensity and degree of a color transition of the polyvalent metal-ion indicator complex from the first color to a second color in response to the metal cation concentration of the aqueous test sample, wherein the color transition is independent of a change in pH and is essentially independent of test sample pH.

19. The method of claim 18 wherein the aqueous test sample is a biological fluid.

20. The method of claim 19 wherein the biological fluid is selected from the group consisting of urine, blood plasma, blood serum, and perspiration.

21. A method of determining the specific gravity of an aqueous sample comprising:
(a) contacting the aqueous sample with an analyte detection device comprising a test pad, said test pad having incorporated therein a reagent composition consisting essentially of:
(i) a polyvalent metal ion;
(ii) an indicator capable of interaction with the polyvalent metal ion to provide a polyvalent metal ion-indicator complex having a first color;
(iii) a buffer; and
(iv) a carrier comprising water, a water miscible alcohol or a mixture thereof, wherein the reagent composition is essentially free of polyelectrolytes; and
(b) determining the specific gravity of the aqueous sample from the intensity and degree of a color transition of the polyvalent metal ion-indicator complex from the first color to a second color in response to the metal cation concentration of the aqueous test sample, wherein the color transition is independent of a change in pH and is essentially independent of test sample pH.

22. A method of determining the specific gravity of an aqueous cation-containing sample comprising:
(a) contacting the aqueous sample with an analyte detection device comprising a test pad having incorporated therein;
(i) a polyvalent metal ion-indicator complex having a first color, said polyvalent metal ion-indicator complex consisting essentially of:
(A) polyvalent metal ion, and
(B) an indicator capable of interacting with the polyvalent metal ion to provide the polyvalent metal ion-indicator complex;
(ii) a buffer; and
(iii) a carrier comprising water, a water miscible alcohol, or a mixture thereof, wherein the test pad is essentially free of polyelectrolytes; and
(b) examining the analyte detection device for a color transition from the first color to a second color in response to the metal cation content of the aqueous sample, wherein the color transition is independent of a change in pH and is essentially independent of test sample pH; and
(c) correlating the color transition to the specific gravity of the aqueous sample.

23. The method of claim 22 wherein the aqueous sample has a specific gravity of about 1.000 to about 1.035.

24. An analyte detection device to determine the specific gravity of an aqueous test sample comprising:
a support strip;
a test pad; and
a reagent composition incorporated into the test pad, said reagent composition consisting essentially of:
(a) a polyvalent metal ion;
(b) an indicator capable of interacting with the polyvalent metal ion to provide a polyvalent metal ion-indicator complex having a first color;
(c) a buffer; and
(d) a carrier comprising water, a water miscible alcohol, or a mixture thereof, wherein the composition is essentially free of polyelectrolytes; and wherein the polyvalent metal ion-indicator complex undergoes a color transition from the first color to a second color in response to the specific gravity of the aqueous test sample, wherein the color transition is independent of a change in pH and is essentially independent of test sample pH.

25. A method of determining the metal cation concentration of an aqueous test sample comprising:
(a) contacting the aqueous test sample with a reagent composition consisting essentially of:
(i) a polyvalent metal ion;
(ii) an indicator capable of interacting with the polyvalent metal ion to provide a polyvalent metal ion-indicator complex having a first color;

(iii) a buffer; and
(iv) a carrier comprising water, a water miscible alcohol or a mixture thereof, and wherein the composition is essentially free of polyelectrolytes; and
(b) determining the metal cation concentration of the aqueous test sample from the intensity and degree of a color transition of the polyvalent metal ion-indicator complex from the first color to a second color in response to the metal cation concentration of the aqueous test sample, wherein the color transition is independent of a change in pH and is essentially independent of test sample pH.

* * * * *